US00PP15389P2

(12) United States Plant Patent
Hooijman

(10) Patent No.: US PP15,389 P2
(45) Date of Patent: Nov. 30, 2004

(54) *PHLOX* PLANT NAMED 'INDICO'

(50) Latin Name: *Phlox paniculata*
Varietal Denomination: Indico

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/783,424

(22) Filed: Feb. 21, 2004

(51) Int. Cl.[7] ..... A01H 5/00
(52) U.S. Cl. ..... Plt./320
(58) Field of Search ..... Plt./320

(56) References Cited

PUBLICATIONS

UPOV ROM 2004/02 citation for 'Indico' GTITM software.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of *Phlox* plant named 'Indico', characterized by its upright plant habit with strong stems; vigorous growth habit; attractive white-colored flowers; freely and uniformly flowering habit; and good postproduction longevity.

1 Drawing Sheet

Botanical classification/cultivar designation: *Phlox paniculata* cultivar Indico.

BACKGROUND OF THE INVENTION

The present Invention relates to a new and distinct cultivar of *Phlox* plant, botanically known as *Phlox paniculata*, and hereinafter referred to by the cultivar name Indico.

The new *Phlox* is a product of a planned breeding program conducted by the Inventor in El Quinche, Pichincha, Ecuador. The objective of the breeding program was to create new vigorous *Phlox* cultivars with white-colored flowers and durable foliage.

The new *Phlox* originated from a cross-pollination made by the Inventor in August, 1999 in El Quinche, Pichincha, Ecuador of a proprietary selection of *Phlox paniculata* identified as Code 3, not patented, as the female, or seed, parent and an unidentified selection of *Phlox paniculata*, not patented, as the male, or pollen, parent. The new *Phlox* was discovered and selected by the Inventor as a flowering plant within the progeny of the stated cross-pollination in a controlled environment in El Quinche, Pichincha, Ecuador. The new *Phlox* was selected on the basis of its white-colored flowers.

Asexual reproduction of the new cultivar by terminal cuttings taken at El Quinche, Pichincha, Ecuador since August, 2000, has shown that the unique features of this new *Phlox* are stable and reproduced true to type in successive generations.

SUMMARY OF THE INVENTION

Plants of the cultivar Indico have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Indico'.

These characteristics in combination distinguish 'Indico' as a new and distinct cultivar:

1. Upright plant habit with strong stems.
2. Vigorous growth habit.
3. Attractive white-colored flowers.
4. Freely and uniformly flowering habit.
5. Good postproduction longevity.

Plants of the new *Phlox* differ from plants of the female parent selection in the following characteristics:

1. Plants of the new *Phlox* are more vigorous than plants of the female parent selection.
2. Plants of the new *Phlox* flower about four or five weeks later than plants of the female parent selection.
3. Plants of the new *Phlox* and the female parent selection differ in flower coloration as plants of the female parent selection have pink-colored flowers.

Plants of the new *Phlox* can be compared to the *Phlox* cultivar Ice Cap, not patented. In side-by-side comparisons conducted in El Quinche, Pichincha, Ecuador, plants of the new *Phlox* differed from plants of the cultivar Ice Cap in the following characteristics:

1. Plants of the new *Phlox* were more vigorous than plants of the cultivar Ice Cap.
2. Plants of the new *Phlox* had longer internodes than plants of the cultivar Ice Cap.
3. Plants of the new *Phlox* had shorter leaves than plants of the cultivar Ice Cap.
4. Plants of the new *Phlox* flowered about four to five weeks later than plants of the cultivar Ice Cap.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox*.

The photograph at the top of the sheet comprises a side perspective view of a typical flowering stem of 'Indico'.

The photograph at the bottom of the sheet is a close-up view of a typical flower of 'Indico'.

DETAILED BOTANICAL DESCRIPTION

The aforementioned photographs, following observations and measurements describe plants grown in El Quinche, Pichincha, Ecuador, in an outdoor nursery and under commercial production practices. Plants were about six months old when the photograph and description were taken. During the production of the plants, day temperatures ranged from 12 to 30° C. and day temperatures ranged from 5 to 12° C. Plants were pinched about two weeks after planting. In the following description, color references are made to The Royal Horticultural Society Colour Chart, 2001 Edition, except where general terms of ordinary dictionary significance are used.

Botanical classification: *Phlox paniculata* cultivar Indico.

Parentage:

*Female parent.*—Proprietary selection of *Phlox paniculata* identified as Code 3, not patented.

*Male parent.*—Unidentified selection of *Phlox paniculata*, not patented.

Propagation:

*Type cutting.*—Terminal vegetative cuttings.

*Time to initiate roots.*—About 10 to 15 days at 17 to 25° C.

*Time to produce a rooted young plant.*—About 28 to 35 days at 17 to 25° C.

*Root description.*—Fine, fibrous; 161C to 158A in color.

*Rooting habit.*—Freely branching; moderately dense.

Plant description:

*Plant form/habit.*—Upright and somewhat outwardly spreading perennial woody shrub; erect inverted triangle; vigorous growth habit.

*Plant height.*—About 84 cm.

*Plant width* (*spread*).—About 29 cm.

*Quantity of stems per year.*—About two; production of stems increases with age of plants.

*Lateral branches.*—Length: About 82 cm. Diameter: About 6 mm. Internode length: About 4.9 cm. Strength: Strong. Texture: Glabrescent. Color: 143C.

*Foliage description.*—Arrangement: Opposite, simple. Length: About 12.6 cm. Width: About 3.3 cm. Shape: Lanceolate to ovate. Apex: Acute to acuminate. Base: Cordate to cuneate. Margin: Entire. Durability: Durable. Texture, upper and lower surfaces: Lamina, sparsely pubescent; margins, bristly. Venation pattern: Pinnate. Color: Developing leaves, upper surface: 137C. Developing leaves, lower surface: 138B to 137D. Fully expanded leaves, upper surface: 137A to 147A. Fully expanded leaves, lower surface: 137C to 138B. Venation, upper surface: 144C. Venation, lower surface: 145C. Petiole length: About 4.6 mm. Petiole diameter: About 4 mm. Petiole color: 144B.

Flower description:

*Flower type/habit.*—Single, rounded salverform flowers arranged in terminal panicles; flowers face upright and outward. Panicles globular or pyramidal in shape. Uniformly and freely flowering habit; about 162 flowers per inflorescence. Flowers fragrant. Flowers not persistent.

*Natural flowering season.*—Continuously flowering from mid-summer through fall. In Ecuador, flowering year round.

*Postproduction longevity.*—Flowers last about 25 days on the plant and about 12 to 14 days as a cut flower.

*Inflorescence height.*—About 24.4 cm.

*Inflorescence diameter.*—About 11.8 cm.

*Flower buds.*—Height: About 2.7 cm. Diameter: About 6 mm. Shape: Fusiform. Color: 145C.

*Flowers.*—Diameter: About 4.1 cm. Depth: About 2.2 cm.

*Petals.*—Quantity per flower: Typically five in a single whorl; petals fused at the base, imbricate. Length: About 1.9 cm. Width: About 2.4 cm. Shape: Roughly spatulate. Apex: Obtuse. Margin: Entire. Aspect: Mostly flat. Texture, upper and lower surfaces: Smooth, glabrous. Color: Developing and fully expanded petals, upper surface: 155D, color becoming closer to 11D with development. Developing and fully expanded petals, lower surface: 155D.

*Sepals.*—Quantity per flower: Typically five in a single whorl, fused; narrow campanulate calyx. Calyx length: About 1.5 cm. Calyx diameter: About 5 mm. Apex: Acuminate. Texture, upper and lower surfaces: Smooth, glabrous. Color: Developing and fully developed sepals, upper surface: 187A to 200A. Developing and fully developed sepals, lower surface: 144B.

*Peduncles.*—Length: About 4.1 cm. Diameter: About 5 mm. Orientation: Erect to about 24° from vertical. Strength: Strong. Color: 143C.

*Pedicels.*—Length: About 9 mm. Diameter: About 1.3 mm. Orientation: Erect to about 43° from vertical. Strength: Moderately strong. Color: 143C.

*Reproductive organs.*—Stamens: Quantity per flower: Typically five. Anther shape: Oval. Anther length: About 3 mm. Anther color: 2D to 4C. Pollen amount: Abundant. Pollen color: 2D to 4C. Pistils: Quantity per flower: Typically one. Pistil length: About 1.6 cm. Stigma shape: Tri-lobed. Stigma color: 145C. Style length: About 1.2 cm. Style color: 145B. Ovary color: 143B.

*Fruits.*—Quantity per flower: Typically one. Type: Capsule. Length: About 8 mm. Diameter: About 6 mm. Texture: Smooth; rugose hen ripe. Color: 138A.

*Seeds.*—Length: About 6 mm. Diameter: About 5 mm. Color: 143B; when dry, N165C.

Disease/pest resistance: Plants of the new *Phlox* have been noted to be resistant to pathogens and pests common to *Phlox*.

Temperature tolerance: Plants of the new *Phlox* have been observed to tolerate temperatures ranging from 0 to 30° C.

It is claimed:

1. A new and distinct cultivar of *Phlox* plant named 'Indico', as illustrated and described.

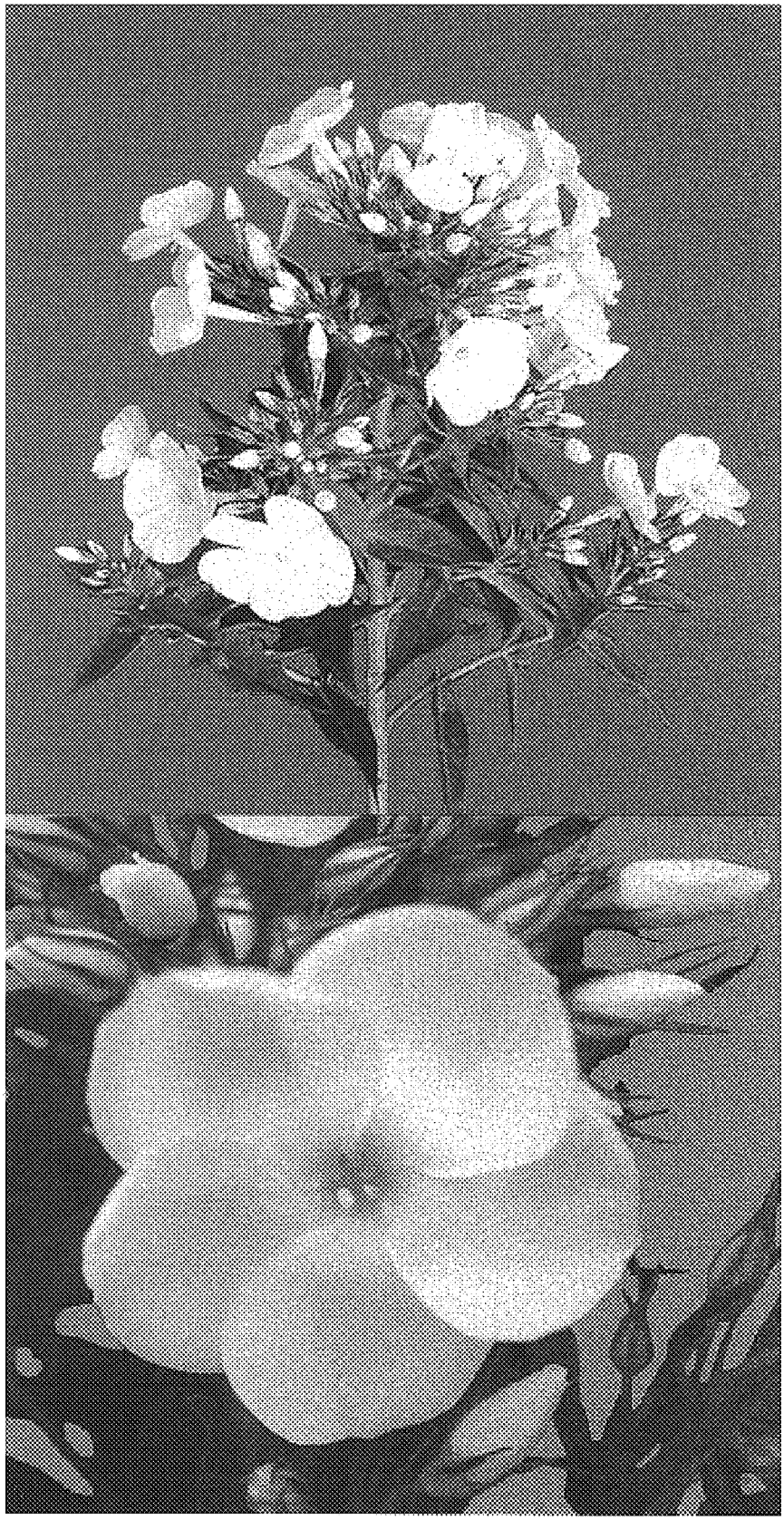

* * * * *